US012636083B2

(12) United States Patent
Kroenke-Hille et al.

(10) Patent No.: US 12,636,083 B2
(45) Date of Patent: May 26, 2026

(54) ASSISTING SUBJECT AND/OR IMPLANT POSITIONING IN MEDICAL IMAGING

(71) Applicant: KONINKLIJKE PHILIPS N.V., Eindhoven (NL)

(72) Inventors: Sven Kroenke-Hille, Hamburg (DE); Jens Von Berg, Hamburg (DE); Stewart Young, Hamburg (DE); Daniel Bystrov, Hamburg (DE); Heiner Matthias Brueck, Pinneberg (DE); Andre Goossen, Eldena (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 191 days.

(21) Appl. No.: 18/710,687

(22) PCT Filed: Nov. 24, 2022

(86) PCT No.: PCT/EP2022/083070
§ 371 (c)(1),
(2) Date: May 16, 2024

(87) PCT Pub. No.: WO2023/099321
PCT Pub. Date: Jun. 8, 2023

(65) Prior Publication Data
US 2025/0025238 A1       Jan. 23, 2025

(30) Foreign Application Priority Data
Nov. 30, 2021     (EP) ..................................... 21211366

(51) Int. Cl.
A61B 6/08          (2006.01)
A61B 6/12          (2006.01)
(Continued)

(52) U.S. Cl.
CPC ...... *A61B 34/10* (2016.02); *A61B 2034/2055* (2016.02)

(58) Field of Classification Search
CPC . A61B 34/10; A61B 2034/2055; A61B 6/505; A61B 6/08; A61B 6/12
See application file for complete search history.

(56) References Cited

U.S. PATENT DOCUMENTS

2007/0225596 A1     9/2007   Justin
2009/0079576 A1     3/2009   Yankelevitz
(Continued)

OTHER PUBLICATIONS

PCT International Search Report, International application No. PCT/EP2022/083070, Mar. 13, 2023.

*Primary Examiner* — Courtney D Thomas
(74) *Attorney, Agent, or Firm* — Larry Liberchuk

(57)          ABSTRACT
The present invention relates to prospective analysis of subject and/or implant positioning. Provided is a computer-implemented method for assisting positioning of a subject having an orthopedic implant in X-ray imaging. The method comprises applying one or more radiofrequency, RF, signals to an anatomy of interest of the subject where the orthopedic implant is located. The method further comprises detecting a response signal and/or signal change in response to the applied RF signal impacting the orthopedic implant and tissue being adjacent to and/or surrounding the implant, and determining, from the detected response signal and/or signal change, an implant positioning estimation relative to an X-ray imaging device. Further, the method comprises determining, from the implant positioning estimation, a feedback being indicative for positioning the X-ray imaging device and the subject to each other with respect to a target positioning, to be provided for assisting the positioning.

15 Claims, 2 Drawing Sheets

(51) Int. Cl.
| | |
|---|---|
| *A61B 34/10* | (2016.01) |
| *A61B 34/20* | (2016.01) |

(56) References Cited

U.S. PATENT DOCUMENTS

| | | | | |
|---|---|---|---|---|
| 2017/0100089 | A1 | 4/2017 | Chang | |
| 2017/0205477 | A1 | 7/2017 | Grodzki | |
| 2018/0247427 | A1 | 8/2018 | Geiger | |
| 2018/0318012 | A1 | 11/2018 | Blau | |
| 2019/0183439 | A1 | 6/2019 | Joerger | |
| 2019/0318497 | A1 | 10/2019 | Zhao | |
| 2020/0375546 | A1 | 12/2020 | Shoudy | |
| 2020/0405194 | A1 | 12/2020 | Sekine | |
| 2021/0077199 | A1* | 3/2021 | Meftah ................ | A61B 34/20 |
| 2021/0080563 | A1* | 3/2021 | Meftah ................ | A61B 90/98 |
| 2024/0070867 | A1 | 2/2024 | Kronke | |

* cited by examiner

ASSISTING SUBJECT AND/OR IMPLANT POSITIONING IN MEDICAL IMAGING

FIELD OF THE INVENTION

The present invention relates to medical imaging, and in particular to a computer-implemented method for assisting positioning of a subject having an implant in X-ray imaging, to a system for assisting positioning of a subject having an implant in X-ray imaging, and to a computer program element for performing the method and/or to control the system.

BACKGROUND OF THE INVENTION

In medical imaging, e.g. in X-ray imaging, appropriate subject positioning can be regarded as being crucial for achieving X-ray images, e.g. musculoskeletal X-ray images etc., of diagnostic quality due to the projective nature of this image modality.

This applies in particular if the positioning of an orthopedic implant is to be imaged, since even slight misposition of the subject can render an X-ray image, with respect to its quality, particularly in terms of the achieved projection, non-diagnostic. This can mitigate the X-ray image suitability for e.g. assessing the implant placement after e.g. a surgery or monitoring possible movements of the implant with respect to the bone over time.

US 2007/0225596 A1 describes an implant fixable relative to a target area within a living body, comprising a transmitter arranged to emit an electromagnetic signal, wherein said electromagnetic signal is adapted to propagate with a wavelength in said living body so that a phase difference of said electromagnetic signal in at least three positions, preferably four, separated by a known distance is detectable by a receiver for tracking variations of a position of the implant relative to said receiver.

US 2009/0079576 A1 describes a system for position matching of a patient for medical imaging includes a set of RFID tags configured to locate a patient position. A set of RFID interrogators are located to receive RFID position information from the set of RFID tags.

US 2018/0318012 A1 relates to processing of a 2D projection image generated during a procedure of fracture treatment of a bone. The computer program element comprises sets of instructions for detecting the reference body in the 2D projection image, detecting at least one element out of the group consisting of an instrument, an implant and an anatomical structure in the 2D projection image, and identifying a current state of the element, determining a state of progress of the procedure of fracture treatment, and providing information regarding steps to be performed next.

SUMMARY OF THE INVENTION

There may, therefore, be a need for improved means for at least assisting positioning of a subject in a manner allowing acquiring a medical image with a desired positioning of an implant therein. The object of the present invention is solved by the subject matter of the independent claims, wherein further embodiments are incorporated in the dependent claims.

According to a first aspect, there is provided a computer-implemented method for assisting positioning of a subject having an implant in X-ray imaging. The method comprises the step of applying one or more radiofrequency (RF) signals to an anatomy of interest of the subject where the implant is located. Further, the method comprises detecting a response signal and/or signal change in response or reaction to the applied RF signal impacting, preferably impinging, the implant and tissue being adjacent to and/or surrounding the implant. In addition, the method comprises determining, from the detected response signal and/or signal change, an implant positioning estimation relative to an X-ray imaging device, and determining, from the implant positioning estimation, a feedback being indicative for positioning the X-ray imaging device and the subject to each other with respect to a target positioning, to be provided for assisting the positioning.

In this way, subject and/or implant positioning can be evaluated, and, if necessary, corrected, even prior to an actual X-ray image acquisition, i.e. without or at least with less radiation exposing to the subject. The above method allows measuring subject and/or implant positioning to give a feedback, such as a confirmation that the positioning is correct, a recommendation and/or action instruction for improving and/or correcting the positioning, or the like, to e.g. an operator, e.g. a radiographer or the like, handling the X-ray imaging for improving the positioning or to device or system for automatically positioning and/or adjusting positioning of e.g. an X-ray tube relative to the subject and/or implant. While a 3D pose and posture of the subject itself could be deduced from e.g. a single or from multiple RGB/grey-value or depth-camera images, classical radar or sonic-reflection images, the 3D pose of the implant cannot be estimated by any of these modalities. In contrast thereto, the above method allows utilizing e.g. reflection and/or absorption properties of RF signals, e.g. RF waves, at and/or in a metallic object, i.e. the implant, and/or the surrounding tissue. e.g. a bone etc., in order to assess positioning, e.g. the pose and/or posture, of metallic orthopedic implants, while keeping the radiation dose to the subject low.

In other words, given an X-ray image, e.g. a musculoskeletal X-ray image featuring an orthopedic implant, assessing its diagnostic quality might be difficult given high patient flow and the resulting time pressure and, in particular, for a novice operator, such as a radiographer. The above method accomplishes an automatic assessment of the subject and/or implant positioning. Further, when assessing image quality manually, individual subjective measures will be applied in general. The above method assists in standardizing image quality, e.g. across a medical imaging department and/or facility. Given that the subject and/or implant positioning deviates from a target or ideal positioning, the above method can assist the radiographer or an automatic positioning system to determine appropriate actions which could improve the image quality. Furthermore, conventional subject positioning can require an iterative process in which the positioning is improved upon the current image if required. These iterations delay the examination at a cost of a higher subject radiation dose than necessary. The above method can be used to optimize the subject's positioning also before the acquisition of an image.

As used herein, the positioning of the subject and/or implant may include providing a specific pose and/or posture relative to the X-ray imaging device, e.g. the X-ray tube, or vice versa. Accordingly, the feedback, which may be output graphically, e.g. via a display etc., via audio, e.g. via a loudspeaker, headphone, etc., or the like, may indicate whether the positioning is already correct or whether and/or how the positioning of the subject and/or implant is to be changed to comply with a target or desired positioning.

As used herein, the one or more RF signals may be applied in e.g. a microwave frequency range and/or in e.g.

the Gigahertz (GHz) range, provided there is a suitable compromise regarding e.g. penetration depth and/or wavelength based spatial resolution limit with respect to the implant and/or the tissue surrounding it. For example, for relevant tissues, such as bone tissue or other tissue types surrounding and/or being adjacent to the implant, the penetration depth may be between approx. 3 cm and 30 cm, and the wavelength may be between approx. 0.1. The one or more RF signals may be emitted from one or multiple mono- or multichromatic sources at one or multiple locations with an intensity chosen to not harm the patient via e.g. local heating. The one or more RF signals may be in a range of 1 GHz to 10 GHz, and/or may be in e.g. a wireless local area network (WLAN) frequency domain, e.g. between approx. 2 GHz and 5 GHz, wherein this is not limited herein. A wavelength may be, for example, in a range of approx. 3 cm to approx. 30 cm. Further, the RF signals may be applied for a relative short period of time, so that the above method may also be applicable to a subject with a pacemaker or the like. It is noted a wavelength-based spatial resolution limit of the above method may be extended, due to prior knowledge. For example, the prior knowledge may be implicitly encoded in the learned model or network weights.

As used herein, the orthopedic implant may be understood as a medical device configured to replace a missing joint or bone or to support a damaged one.

Further, the detected response signal and/or signal change may be derived passively. i.e., by omitting a sender or transmitting device within or inside the anatomy of interest, from detecting e.g. reflection and/or absorption properties of radiofrequency RF waves at and/or in the implant, which may be made of or may comprise e.g. a metal material etc., and/or in a tissue surrounding the implant. The detection may utilize a suitable detector or sensor, such as an RF receiver, e.g. in form of a coil, or the like.

The image-acquisition geometry. e.g. a radiation source and detector constellation, relative to the detected RF signal may be either been known, calibrated or measured. For example, the image-acquisition geometry may be determined using an optical image, e.g. a camera image or video.

The method may preferably be performed by use of a system according to the second aspect. Further, the method steps may be implemented in hardware and/or software.

According to an embodiment, the feedback may comprise an action instruction if the implant positioning is determined to deviate from the target positioning, and otherwise a confirmation that the positioning is correct. In other words, if the subject and/or implant positioning is determined to comply with the target positioning, the feedback may confirm correct or target positioning. In this way, the operator may receive the confirmation of correct positioning, or, in case of sub-optimal positioning, instructions how to achieve it from the current positioning determined. The action instruction may comprise a guidance how to achieve target positioning from the current positioning.

In an embodiment, the detected response signal and/or signal change may be based on or may comprise one or more reflection and/or absorption properties of the one or more RF signals at the implant and/or the tissue. For example, the one or more RF signals may be absorbed and/or reflected to different extents by different materials and tissues, and this difference is measured by a detector or sensor. By way of example, the reflection and/or absorption properties of the joint of interest and its implant may be detected via one or multiple RF receivers, e.g. a coil or the like. By way of example of an implant in e.g. a tibia bone, the response signal and/or signal change, e.g. due to reflection and/or absorption properties, of one or more RF signals at the proximal plateau of the implant may be taken into account for positioning one or more receivers at positions with predictive power for assessing the implant pose. This allows a measuring to be carried out by harmless electromagnetic radiation, which enables a reconstruction of the current subject and/or implant positioning. In this way, the radiation to which the patient is exposed can be kept low.

According to an embodiment, the detected response signal and/or signal change may be detected and/or determined in a spatial distribution manner. Based on this determination, the pose and/or posture may be estimated, predicted and/or reconstructed in spatial relation, e.g. in 3D. In this way, the positioning can be more accurately.

In an embodiment, the positioning estimation may be determined by feeding the detected response signal and/or signal change into a physical simulation model of RF scattering and RF absorption at the implant and/or the tissue, and calculating the positioning estimation therefrom. In other words, the measured one or more RF signals, i.e. the detected response signal and/or signal change, may then be fed into a processor for predicting the pose and/or posture of the implant. The processor may be configured to provide a physical simulation, i.e. run the physical simulation model, of the RF scattering at the implant and its absorption. In this way, the pose and/or posture of the implant can be estimated, predicted, etc.

In an embodiment, the physical simulation model may be further fed with a 3D implant model of the implant. The 3D implant model may be similar to or of the implant. For example, the 3D implant model may be assigned to a specific implant type that at least largely corresponds to the implant type of the subject to be imaged. The 3D implant model may be provided as e.g. a 3D CAD-model. Thereby, the 3D implant model may be deformable to be adapted to the implant actually present in the given subject to be imaged. Optionally, the 3D implant model may be of the implant actually present in the given subject. Optionally, it may be configured to estimate a 3D pose and/or posture of the implant.

According to an embodiment, the positioning estimation may be determined by feeding the detected response signal and/or signal change into an implant pose and/or posture machine-learning model, which is trained by training data of a reflected and/or absorbed RF signal with known patient and/or implant positioning, and the implant positioning estimation may be calculated therefrom. For example, the implant pose and/or posture machine-learning model may be a deep learning forward-model that may be trained on real or simulated data of reflected and/or absorbed RF signals with known implant pose to estimate and/or predict the latter. The model may be trained to predict from RF reflection and/or absorption at a specific or various implant type, wherein a wavelength-based spatial resolution limit of the above method may be extended, since there is prior knowledge implicitly encoded in the learned model or network weights. In this way, the pose and/or posture of the implant can be estimated, predicted, etc.

In an embodiment, the method may further comprise comparing the implant positioning estimation with a further implant positioning determination derived from X-ray image data of the subject including the implant, wherein the comparison may be used to adapt the above physical simulation model or to adapt the above implant pose machine-learning model. This can also be understood as verification of the above method, which can be performed once or from time to time. In this way, each model can be trained, re-trained, fine-tuned, etc.

According to an embodiment, the method may further comprise:

determining a subject positioning estimation, which differs from the implant positioning estimation by having less or no penetration into the subject; and combining the implant positioning estimation and the subject positioning estimation with each other;

wherein the feedback to be provided is determined from the combined implant positioning estimation and subject positioning estimation.

For example, the pose and/or posture of the implant derived based on the one or more RF signals may be combined with an estimated pose and/or posture of the subject, which may be determined based on a signal different to the one or more signals, such as optical detection, in order to apply compromise criteria for positioning quality or accuracy that take a variability in the relative positions of the implant and the tissue, e.g. bone(s), into account.

In an embodiment, the subject positioning estimation may be determined based on patient pose and/or posture measurement data derived from one or more of an optical camera, an RGB camera, a depth camera, a radar measuring device, and a sonic echo measuring device.

According to an embodiment, the method may be performed prior to the actual X-ray imaging. In this way, the method provides a prospective analysis of subject and/or implant positioning.

In an embodiment, the method may be performed during X-ray imaging, continuously monitoring implant and/or subject positioning. Thereby, the method further comprises generating a trigger signal for X-ray image acquisition if the monitored implant positioning and/or subject positioning meets an image acquisition criterion. In this way, continuous monitoring of the subject and/or implant positioning can be utilized for finding the optimal moment of image acquisition. For example, if the subject moves the limb of interest after seemingly accomplished patient positioning, the monitoring can indicate a sub-optimal positioning. Thereby, the radiographer can postpone the image acquisition either until the patient moved into a better positioning or until he/she has been re-positioned by the radiographer. Further, the trigger signal can be used for automatic imaging.

According to a second aspect, there is provided a system for assisting positioning of a subject having an implant in X-ray imaging. The system comprises:

a radiofrequency, RF, emitter, configured to apply one or more RF signals to an anatomy of interest of the subject where the implant is located;

an RF receiver, configured to detect a response signal and/or a signal change in response to the applied RF signal impacting the implant and tissue being adjacent to and/or surrounding the implant; and a processor, configured to:

determine, from the detected response signal and/or signal change, an implant positioning estimation; and determine, from the implant positioning estimation, a feedback being indicative for positioning the X-ray imaging device and the subject to each other, to be provided for assisting the positioning.

The system is configured to carry out the method of the first aspect. Accordingly, the system allows the subject and/or implant positioning to be evaluated, and, if necessary, corrected, even prior to an actual X-ray image acquisition, i.e. without or at least with less radiation exposing to the subject.

According to an embodiment, wherein the one or more RF signals are emitted in a Gigahertz frequency domain. In this way, the system allows a penetration depth and wavelength suitable for detecting the implant and estimating its positioning.

In an embodiment, the system may further comprise a communication interface configured to output the feedback. For example, the communication interface may be configured to provide the feedback graphically, in audio, or the like. It may comprise or may connected to a display, loudspeaker, or the like. In this way, the system may improve positioning of the subject and/or implant with precise instruction.

According to a third aspect, there is provided a computer program element, which when executed by a processor is configured to carry out the method of the first aspect, and/or to control a system according to the second aspect.

According to a fourth aspect, there is provided a computer-readable storage or transmission medium, which has stored or which carries the computer program element according to the third aspect.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
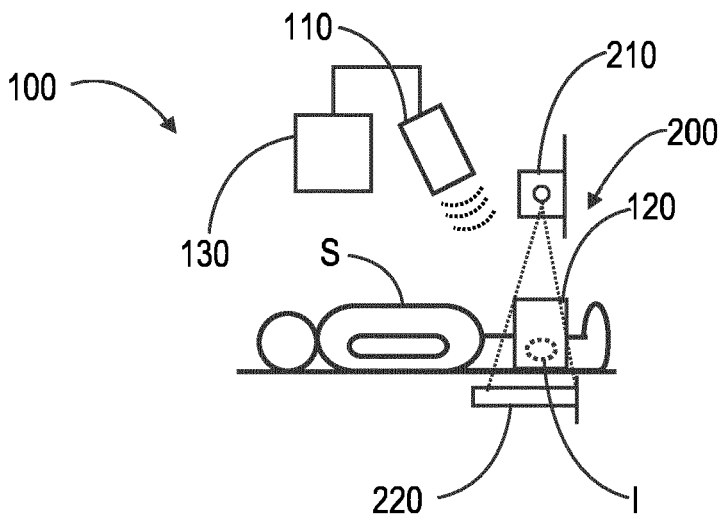
FIG. 1 shows in a schematic block diagram a system for assisting positioning of a subject having an implant in X-ray imaging, according to an embodiment.

FIG. 1 shows in a schematic block diagram a system 100 that is configured to assist positioning of a subject S having an implant I, particularly orthopedic implant I, in X-ray imaging, the latter being be carried out using, for example, an X-Ray device 200 with a radiation source 210 and a detector 220. The system 100 comprises a radiofrequency (RF) emitter 110, an RF receiver 120 and a processor 130.

The system 100 can be used for a prospective analysis for subject positioning prior to the actual X-ray imaging, as indicated in FIG. 1, which shows indicates by an arrow that the positioning is analyzed first and only then the image is acquired. It should be noted that positioning also takes place in a preparation phase of the subject S, which precedes the image acquisition phase, in a different space than the image acquisition phase, such as a preparation room. In addition, it should be noted that the subject S may also already be at or in the X-ray device 200 so that the system 100 and the X-ray device 200 are combined, e.g. to be arranged at a same place, and the subject S does not need to be moved from the system 100 to the X-ray device 200.

The RF emitter 110 is configured to apply one or more RF signals to an anatomy of interest of the subject S where the implant I is located. Preferably, the RF emitter 110 is located outside of the anatomy of interest. For example, the RF emitter 110 may comprise or may be formed by one or multiple mono- or multichromatic sources. Further, by way of example, the one or more RF signals may be applied in e.g. a microwave frequency range and/or in e.g. the Giga-hertz (GHz) range, e.g. in a wireless local area network (WLAN) frequency domain, e.g. between approx. 2 GHz and 5 GHz.

The RF receiver 120 is configured to detect a response signal and/or a signal change in response to the applied RF signal impacting the implant I and tissue being adjacent to and/or surrounding the implant. Preferably, the RF receiver 120 is located outside of the anatomy of interest. The implant I may be made of or may comprise e.g. a metal material etc., and/or in a tissue surrounding the implant. The detection may utilize a suitable detector or sensor, such as an RF receiver, e.g. in form of a coil, or the like.

The processor 130 is configured to determine, from the detected response signal and/or signal change, an implant positioning estimation. Further, the processor 130 is config-ured to determine, from the implant positioning estimation, a feedback being indicative for positioning the X-ray imag-ing device 200 and the subject S to each other, to be provided for assisting the positioning.

Optionally, the processor 130 may be configured to pro-vide the feedback during X-ray imaging for continuously monitoring implant and/or subject positioning. Thereby, the processor 130 may be configured to generate a trigger signal for X-ray image acquisition if the monitored implant posi-tioning and/or subject positioning meets an image acquisi-tion criterion. For example, the processor 130 may be configured to generate the trigger signal if the positioning complies with a target positioning.

Figure 2:
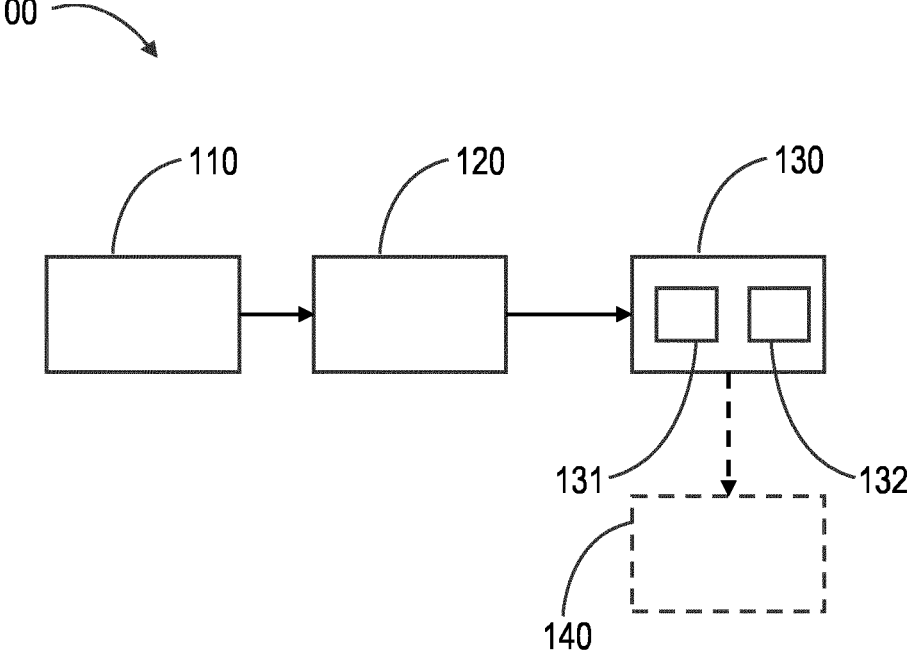
FIG. 2 shows in a schematic block diagram a determination of a positioning estimation based on signal processing, according to one embodiment.

FIG. 2 shows in a schematic block diagram a determina-tion of a positioning estimation based on signal processing, according to one embodiment. The RF emitter 110 emits one or more RF signals towards the subject S, wherein the RF receiver 120 detects the response signal(s) and/or a signal change in response to the applied RF signal.

Optionally, the processor 130 may be configured to execute a physical simulation model 131 of RF scattering and RF absorption at the implant and/or the tissue for determining the positioning estimation by feeding the detected response signal and/or signal change into the physi-cal simulation model. Thereby, the processor 130 may be configured to calculate the positioning estimation therefrom. Further optionally, the processor 130 may be configured to feed the physical simulation model with a 3D implant model of the implant. The 3D implant model may be similar to or of the implant. For example, the 3D implant model may be assigned to a specific implant type that at least largely corresponds to the implant type of the subject to be imaged. The 3D implant model may be provided as e.g. a 3D CAD-model.

Further optionally, the processor 130 may be configured to provide a physical simulation, i.e. run the physical simu-lation model, of the RF scattering at the implant and its absorption.

Optionally, the processor 130 may be configured to execute an implant pose and/or posture machine-learning model 132, which is trained by training data of a reflected and/or absorbed RF signal with known implant positioning estimation, by feeding the detected response signal and/or signal change into the implant pose and/or posture machine-learning model. Thereby, the processor 130 may be config-ured to calculate the implant positioning estimation there-from. For example, the implant pose and/or posture machine-learning model may be a deep learning forward-model that may be trained on real or simulated data of reflected and/or absorbed RF signals with known implant pose to estimate and/or predict the latter. The model may be trained to predict from RF reflection and/or absorption at a specific or various implant types.

Further, as shown in FIG. 2, the system 100 may comprise a communication interface 140 configured to output the feedback. For example, the communication interface 140 may be configured to provide the feedback graphically, in audio, or the like. It may comprise or may connected to a display, loudspeaker, or the like.

Figure 3:
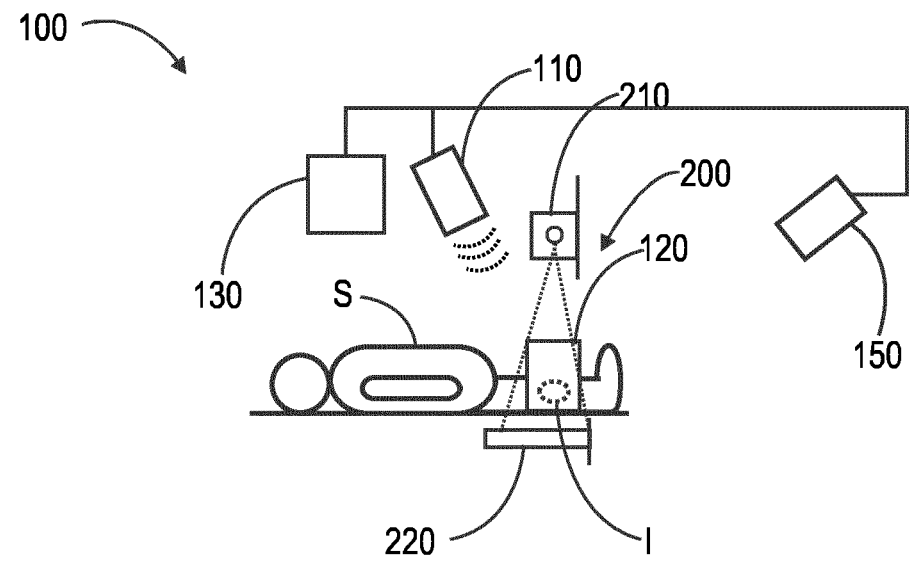
FIG. 3 shows in a schematic block diagram a system for assisting positioning of a subject having an implant in X-ray imaging, according to an embodiment.

FIG. 3 shows in a schematic block diagram the system 100 of FIG. 2, further comprising an optical device 150 for detecting positioning data of the subject S. From a functional perspective, the optical device differs from the RF emitter 110 and RF receiver 120 by having less or no penetration into the subject S. The optical device 150 may comprise or may be formed by one or more of an optical camera, an RGB camera, a depth camera, a radar measuring device, and a sonic echo measuring device. Thereby, the processor 130 is configured to determine a subject positioning estimation based on patient pose and/or posture measurement data derived from the optical device 150 and to combine the implant positioning estimation and the subject positioning estimation with each other, and the feedback to be provided is determined from the combined implant positioning esti-mation, which utilizes the response signal and/or signal change of the one or more RF signals, and subject position-ing estimation.

Figure 4:
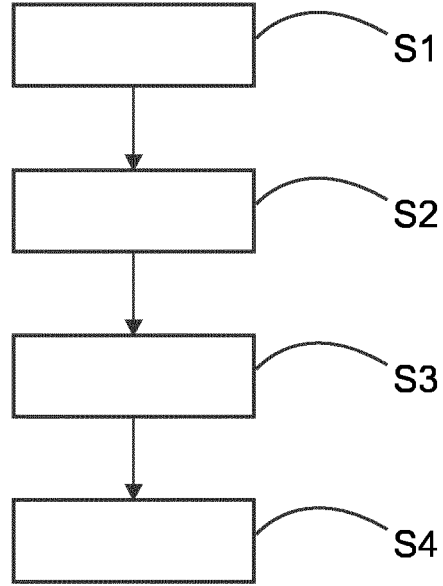
FIG. 4 shows in a flow diagram a method

FIG. 4 shows in a flow diagram a method for assisting positioning of a subject having an implant in X-ray imaging. The method is carried out by utilizing the system 100 described above.

In a step S1, the RF emitter 110 emits one or more RF signals to be applied to an anatomy of interest of the subject S where the implant I is located.

In a step S2, the RF receiver 120 detects a response signal and/or signal change in response to the applied RF signal impacting the implant I and tissue. e.g. bone(s), being adjacent to and/or surrounding the implant I.

In a step S3, the processor 130 determines, from the detected response signal and/or signal change, an implant positioning estimation relative to the X-ray imaging device 200.

In a step S4, the processor 130 determines, from the implant positioning estimation, a feedback being indicative for positioning the X-ray imaging device 200 and the subject to each other with respect to a target positioning, to be provided for assisting the positioning.

Optionally, the detected response signal and/or signal change is based on or comprises one or more reflection and/or absorption properties of the one or more RF signals at the implant and/or the tissue. It should be noted that the reflection and/or absorption characteristics of the RF signal due to material properties of the implant and/or surrounding tissue allow determination of, or inference or estimation of, the pose, posture, location, orientation, alignment, etc. Further optionally, the detected response signal and/or signal change is detected and/or determined in a spatial distribution manner.

For example, the positioning estimation is determined by feeding the detected response signal and/or signal change into a physical simulation model of RF scattering and RF absorption at the implant and/or the tissue, and calculating the positioning estimation therefrom. Alternatively, or additionally, the positioning estimation is determined by feeding the detected response signal and/or signal change into an implant pose machine-learning model, e.g. a fully-connected neural network, which is trained by training data of a reflected and/or absorbed RF signal with known implant positioning, and calculating the implant positioning estimation therefrom.

Optionally, when determining and/or generating the feedback, a distinction is made as to whether and how exactly the positioning matches the target positioning or in which respect the positioning deviates from it. If the positioning does not match the target positioning, the feedback is determined to guide e.g. the operator how to achieve the target positioning from the positioning determined with the above method.

As indicated in FIG. 3, optionally, the method further comprises comparing the implant positioning estimation with a further implant positioning determination derived from X-ray image data of the subject including the implant, wherein the comparison is used to adapt the physical simulation model or to adapt the implant pose machine-learning model. For example, a subject positioning estimation, which differs from the implant positioning estimation by having less or no penetration into the subject may be determined, wherein the implant positioning estimation and the subject positioning estimation are combined with each other, and wherein the feedback to be provided is determined from the combined implant positioning estimation and subject positioning estimation.

Further optionally, the above method is performed during X-ray imaging, continuously monitoring implant and/or subject positioning, wherein the processor 130 may be configured to generate a trigger signal for X-ray image acquisition if the monitored implant positioning and/or subject positioning meets an image acquisition criterion.

In another exemplary embodiment, a computer program or computer program element is provided that is characterized by being configured to execute the method steps of the method according to one of the preceding embodiments, on the system 100.

The computer program element might therefore be stored to be executed by the processor 130, which might also be part of an embodiment. This processor unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

The computer program element may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 system
    110 RF emitter
    120 RF receiver
    130 processor
    140 communication interface
    150 optical detection device
    200 X-ray device
    210 radiation source
    220 detector

The invention claimed is:

1. A computer-implemented method for assisting positioning of a subject having an orthopedic implant in X-ray imaging, comprising:

applying one or more radiofrequency (RF) signals to an anatomy of interest of the subject where the orthopedic implant is located;

detecting a response signal and/or signal change in response to the applied RF signal impacting the orthopedic implant and tissue being adjacent to and/or surrounding the implant;

determining, from the detected response signal and/or signal change, an implant positioning estimation relative to an X-ray imaging device; and determining, from the implant positioning estimation, a feedback being indicative for positioning the X-ray imaging device and the subject to each other with respect to a target positioning, to be provided for assisting the positioning.

2. The method of claim 1, wherein the feedback comprises an action instruction if the implant positioning is determined to deviate from the target positioning, or a confirmation that the positioning is correct.

3. The method of claim 1, wherein the detected response signal and/or signal change is based on or comprises one or more reflection and/or absorption properties of the one or more RF signals at the orthopedic implant and/or the tissue.

4. The method of claim 1, wherein the detected response signal and/or signal change is detected and/or determined in a spatial distribution manner.

5. The method of claim 1, wherein the positioning estimation is determined by feeding the detected response signal and/or signal change into a physical simulation model of RF scattering and/or RF absorption at the orthopedic implant and/or the tissue, and calculating the positioning estimation therefrom.

6. The method of claim 5, wherein the physical simulation model is further fed with a 3D model of the orthopedic implant.

7. The method of claim 1, wherein the positioning estimation is determined by feeding the detected response signal and/or signal change into an implant pose machine-learning model, which is trained by training data of a reflected and/or absorbed RF signal with known implant positioning, and calculating the implant positioning estimation therefrom.

8. The method of claim 1, further comprising:

determining a subject positioning estimation; and combining the implant positioning estimation and the subject positioning estimation with each other;

wherein the action instruction to be provided is determined from the combined implant positioning estimation and subject positioning estimation.

9. The method of claim 8, wherein the subject positioning estimation is determined based on patient pose and/or posture measurement data derived from one or more of an optical camera, an RGB camera, a depth camera, an infrared camera, a radar measuring device, and a sonic echo measuring device.

10. The method of claim 1, wherein the method is performed prior to the actual X-ray imaging.

11. The method of claim 1, wherein the method is performed during X-ray imaging, continuously monitoring implant and/or subject positioning, the method further comprising:

generating a trigger signal for X-ray image acquisition if the monitored implant positioning and/or subject positioning meets an image acquisition criterion.

12. A system for assisting positioning of a subject having an orthopedic implant in X-ray imaging, the system comprising:

an radiofrequency (RF) emitter configured to apply one or more RF signals to an anatomy of interest of the subject where the orthopedic implant is located;

an RF receiver configured to detect a response signal and/or a signal change in response to the applied RF signal impacting the orthopedic implant and tissue being adjacent to and/or surrounding the orthopedic implant; and a processor configured to:

determine, from the detected response signal and/or signal change, an implant positioning estimation; and determine, from the implant positioning estimation, a feedback being indicative for positioning the X-ray imaging device and the subject to each other, to be provided for assisting the positioning.

13. The system of claim 12, wherein the one or more RF signals are emitted in a Gigahertz frequency domain.

14. The system of claim 12, further comprising a communication interface configured to output the feedback.

15. A non-transitory computer-readable medium for storing executable instructions, which cause a method for assisting positioning of a subject having an orthopedic implant in X-ray imaging to be performed, the method comprising:

applying one or more radiofrequency (RF) signals to an anatomy of interest of the subject where the orthopedic implant is located;

detecting a response signal and/or signal change in response to the applied RF signal impacting the orthopedic implant and tissue being adjacent to and/or surrounding the implant;

determining, from the detected response signal and/or signal change, an implant positioning estimation relative to an X-ray imaging device; and determining, from the implant positioning estimation, a feedback being indicative for positioning the X-ray imaging device and the subject to each other with respect to a target positioning, to be provided for assisting the positioning.

* * * * *